(12) United States Patent
Flach et al.

(10) Patent No.: US 12,016,995 B2
(45) Date of Patent: Jun. 25, 2024

(54) REMOVABLE ENCLOSURE FOR A NEGATIVE PRESSURE WOUND THERAPY DEVICE

(71) Applicant: Mölnlycke Health Care AB, Gothenburg (SE)

(72) Inventors: Niclas Flach, Alingsås (SE); David Valham, Västra Frölunda (SE); Stefan Kidborg, Ytterby (SE); Jonas Nordborg, Gothenburg (SE)

(73) Assignee: Mölnlycke Health Care AB, Gothenburg (SE)

( * ) Notice: Subject to any disclaimer, the term of this patent is extended or adjusted under 35 U.S.C. 154(b) by 0 days.

(21) Appl. No.: 18/550,149

(22) PCT Filed: Mar. 14, 2022

(86) PCT No.: PCT/EP2022/056547
§ 371 (c)(1),
(2) Date: Sep. 12, 2023

(87) PCT Pub. No.: WO2022/200103
PCT Pub. Date: Sep. 29, 2022

(65) Prior Publication Data
US 2024/0042121 A1 Feb. 8, 2024

(30) Foreign Application Priority Data
Mar. 22, 2021 (EP) .................................. 21164071

(51) Int. Cl.
*A61M 1/00* (2006.01)

(52) U.S. Cl.
CPC .............. *A61M 1/96* (2021.05); *A61M 1/984* (2021.05); *A61M 2205/42* (2013.01)

(58) Field of Classification Search
CPC ...... A61M 1/00; A61M 1/90; A61M 2205/42; A61M 35/00; A61M 1/0058; A61M 1/77;
(Continued)

(56) References Cited

U.S. PATENT DOCUMENTS 8,127,888 B1 * 3/2012 Mah .................. G10K 11/22
123/184.53
8,550,308 B2 * 10/2013 Py ..................... B65D 77/067
222/207
(Continued)

FOREIGN PATENT DOCUMENTS

CN 211222322 U * 9/2019
CN 214387497 U * 12/2020
(Continued)

OTHER PUBLICATIONS

International Search Report and Written Opinion were mailed on Jun. 27, 2022 by the International Searching Authority for International Application No. PCT/EP2022/056547 filed on Mar. 14, 2022 and published as WO 2022/200103 (Applicant: Molnlycke Health Care AB) (10 pages).

*Primary Examiner* — Rebecca E Eisenberg
*Assistant Examiner* — Hans Kaliher
(74) *Attorney, Agent, or Firm* — Ballard Spahr LLP

(57) ABSTRACT

The present disclosure generally relates to a removable enclosure for a mobile negative pressure wound therapy (NPWT) device, where the enclosure is arranged to reduce unwanted noise from a pump comprised with the negative pressure pump. The enclosure is specifically useful when operating the NPWT device during nighttime.

20 Claims, 3 Drawing Sheets

(58) Field of Classification Search
CPC ........ A61M 1/915; A61M 1/96; A61M 1/984;
A61F 13/00; A61F 13/02; A61F 13/0216;
A61H 9/0057
See application file for complete search history.

(56) References Cited

U.S. PATENT DOCUMENTS

| | | | |
|---|---|---|---|
| 10,328,188 B2* | 6/2019 | Deutsch | A61M 1/98 |
| 2002/0134378 A1* | 9/2002 | Finnegan | A61M 16/021 |
| | | | 128/200.24 |
| 2013/0110058 A1* | 5/2013 | Adie | A61M 1/962 |
| | | | 604/319 |
| 2014/0343518 A1 | 11/2014 | Riesinger | |
| 2019/0365966 A1* | 12/2019 | Bächler | F04B 39/0044 |

FOREIGN PATENT DOCUMENTS

| | | |
|---|---|---|
| WO | WO 2013/171585 A2 | 11/2013 |
| WO | WO 2020/005532 A1 | 2/2020 |

* cited by examiner

REMOVABLE ENCLOSURE FOR A NEGATIVE PRESSURE WOUND THERAPY DEVICE

TECHNICAL FIELD

The present disclosure generally relates to a removable enclosure for a mobile negative pressure wound therapy (NPWT) device, where the enclosure is arranged to reduce unwanted noise from a pump comprised with the negative pressure pump. The enclosure is specifically useful when operating the NPWT device during nighttime.

BACKGROUND

Negative pressure wound therapy (NPWT) is a technique that promotes healing of e.g. surgical, acute, and chronic wounds by the application of a sub-atmospheric pressure to the wound, using a negative pressure pump. The NPWT technique also permits less outside disturbance of the wound as well as for transportation of excess fluids away from the wound site. Generally, the NPWT technique has until now mainly been applied to a patient while in a hospital environment. However, recent product development now allows the technique to be used by a patient in a home environment.

When an NPWT device is used in such a home environment, it may be possible that the NPWT device is not operated and monitored by professional users, as compared to when the NPWT device is used in the mentioned hospital environment. Thus, it is desirable to further simplify the operational use of the NPWT device, for minimizing any errors in use and handling.

Introducing the NPWT device in the home environment may in some situations have further implications on the patient and/or e.g. a partner of the patient. Specifically, when the negative pressure pump is operating, the pump may generate a noise that may be perceived as disturbing for the patient and/or the partner of the patient.

One example of an NPWT device trying to mitigate this problem is disclosed in U.S. Pat. No. 8,257,328, where a direct current (DC) motor-driven pump comprised within a housing of the NPWT device is operated to achieve the negative pressure. In U.S. Pat. No. 8,257,328, a vibration damping tape, e.g., visco-elastic damping tape, may be applied to an outer surface of the pump to reduce vibration and its associated noise. The pump may also be contained within a sub-housing arranged within the housing of the NPWT device, where the sub-housing may be hollow or formed entirely of open cell molded foam, e.g., used as a silencer to provide sound mitigation by reducing the sound energy of during operation of the pump.

The solution presented in U.S. Pat. No. 8,257,328, specifically by arranging the pump within the mentioned sub-housing, generally reduces the level of noise generated during operation of the NPWT device. However, to achieve a desirable noise mitigating effect it will be necessary to introduce a substantial amount of the foam within the housing of the NPWT device, in turn result in a bulky NPWT device. Accordingly, there appears to be desirable to provide for other measures in mitigating the generated noise, while still ensuring that the NPWT device is safe to operate within the mentioned home environment.

SUMMARY

In view of above-mentioned and other drawbacks of the prior art, it is an object of the present disclosure to provide improvements in relation to efficient and safe operation of a NPWT device operating to establish a negative pressure within the sealed space formed by a wound cover in relation to a wound site.

According to an aspect of the present disclosure, it is therefore provided a removable enclosure for a mobile negative pressure wound therapy (NPWT) device, the NPWT device comprising a negative pressure pump arranged within a housing of the NPWT device and connected to wound cover using a conduit, wherein the removable enclosure comprises a first housing section, and a second housing section, wherein the second housing section is arranged to join the first housing section to enclose the NPWT device, wherein the first and the second housing section each comprises an outer shell material and an inner insulation material, at least one of the first or the second housing section is provided with an opening for passage of the conduit through a wall of the first housing section, the second housing section is provided with a sound duct extending through the outer shell material and the inner insulation material, and the sound duct is positioned to propagate a sound emitted by a sound generating device comprised with the NPWT device to an outside of the removable enclosure, wherein the sound emitted by the sound generating device is indicative of a state of the NPWT device.

The present disclosure is based upon the realization that further measures are needed to ensure that the operation of the NPWT device does not disturb the patient and/or e.g. a partner of the patient. This is of specific importance during nighttime, when even in comparison low-level noise can be disturbing for the patient, and possibly the patient's partner if sharing the same bedroom. This is line with the present disclosure solved by providing the patient with a removable enclosure for the NPWT device, where the intention is to use the removable enclosure when the extra sound mitigation is needed. Nighttime usage of the removable enclosure is thus just an example of when such extra sound mitigation is advantageously applied. The combination of the forming the two housing sections from a combination of an outer shell material and an inner insulation material has surprisingly shown to greatly reduce the noise level of the NPWT device to such an extent that the patient and/or the partner of the patient do not perceived to be disturbed, even in a normal situation where the negative pressure pump is operation in an irregular manner (meaning that the noise level will be fluctuating over time).

It is generally desirable, but in some embodiments not absolutely necessary, to form the inner insulation material to match a shape of the NPWT device. The NPWT device will in such an embodiment have a "snug fit" to the inner insulation material, similar to how a camera may be positioned in a specifically adapted camera case. The combined insulation material for the first and the second housing section may in such an embodiment be formed to have a hollow portion towards the center of the removable enclosure, where the hollow portion matches the shape of the NPWT device.

Furthermore, since the operation of the NPWT device is in the mentioned home environment and not supervised by a skilled operator (such as e.g. a nighttime nurse), it is necessary to ensure that a sound indicative of a state of the NPWT device is still allowed to propagate to an outside of the removable enclosure. This is line with the present disclosure solved by introducing a sound duct extending through the outer shell material and the inner insulation material. The sound duct will thus at one end be positioned towards the NPWT device, and at the other end facing out of the removable enclosure. The end positioned towards the NPWT device is preferably arranged in relation to an area at the NPWT device where a volume of the sound generated by the sound generating device is as large as possible. Such an area may for example be defined by a sound outlet provided in a surface of the NPWT device, where the sound outlet possibly could be arranged to coincide with a position of the sound generating device at a printed circuit board (PCB) of the NPWT device.

It may however as an alternative be possible to allow the sound generating device to use a housing of the NPWT device to form part of the sound generating device. In such an embodiment it may thus be desirable to arrange the sound duct to engage and/or contact with the housing of the NPWT device.

To further heighten the sound mitigation effect of using the removable enclosure it may be desirable to ensure that the first housing section and the second housing section are adapted to at least partly overlap and to completely encloses the NPWT device. It is of course necessary to ensure that the conduit is allowed to pass through e.g. a wall of the first and/or the second housing section of the removable enclosure. Thus, the conduit should not be interpreted as forming part of the NPWT device. Rather, the conduit forms together with the NPWT device and a wound cover part of a wound treatment system as will be discussed below in relation to the detailed description.

In one embodiment it may be possible to arranged each of the first and the second housing section as an open box having five sides (an open top with a bottom and four walls). The second housing section may be made slightly larger as compared to the first housing section, where the openings are arranged towards each other when joined and where the first housing section is arranged partly within the second housing section. The first and the second housing section will thus together form a closed box, where one section can be seen as a lid and the other section as a bottom. It is as such desirable to arrange the lid to tightly fit to the bottom such that a minimal amount of noise is released at an interface between the bottom and the lid.

To ensure that the conduit is allowed to pass through the wall of the first and/or the second housing section of the removable enclosure it may accordingly be desirable to arrange the opening for passage conduit as a slot within the wall of the first and/or second housing section of the removable enclosure. The opening within the wall may alternatively be formed as a slit or a notch. The slot/slit/notch is desirably selected to ensure that the conduit is not "squeezed". Typically, a squeezed conduit could potentially reduce a suction power of the NPWT device.

It may in some embodiments be desirable to also introduce a slot within a wall of the second housing section, wherein the slots align when the first housing section and the second housing section are joined together. Such an embodiment may be implemented with a desire to ensure that the NPWT device is "correctly" positioned within the removable enclosure, ensuring that the NPWT device is tightly fitted within the removable enclosure and align with possible hollow portions of the respective first and second housing sections.

It may generally be desirable to select the outer shell material to be of paper or plastic. From a cost perspective it may be suitable to select a paper material, such as for example of cardboard. An outer shell material formed as a sandwich structure comprising a paper interior has shown specifically suitable to provide the noise mitigating effects as desired in accordance to the present disclosure. In one embodiment a thickness of the outer shell material is at least 2 mm.

As mentioned above, it is generally desirable to form the inner insulation material to match the shape of the NPWT device, thereby maximizing a volume of the inner insulation material provided within the removable enclosure when the removable enclosure is closed around the NPWT device. One type of suitable inner insulation material is a polymer material, such as for example having a cell structure. A possible suitable inner insulation material may as such be a foam material.

To achieve a desirable amount of noise damping it is in one embodiment preferred to select a thickness of the inner insulation material to be at least 5 mm, preferably at least 10 mm. The thickness of the inner insulation material may also as an alternative be selected depending on desired amount of attenuation of the noise from the negative pressure pump during its operation. In a preferred embodiment the attenuation of the noise from the negative pressure pump is at least 4 dBa, preferably at least 6 dBa.

As discussed above and defined in accordance to the present disclosure, the sound duct extending through the outer shell material and the inner insulation material of the second housing section. It may in some embodiments be desirable to reduce any sound damping effect of the inner insulation material by arranging the sound duct to comprise a duct material that is selected to be different from the inner insulation material. That is, if for example the inner insulation material is a foam material, the foam material may dampen sound waves propagating through the sound duct. Arranging a wall of the sound duct to have more dense material properties may greatly reduce such a dampening effect. However, the fact that the duct material that is selected to be different from the inner insulation material should be interpreted in the broadest sense, also including an embodiment where a material property of the inner insulation material has been altered. As an example of such an alteration, it could for example be possible to heat treat the inner insulation material at a surface towards the sound duct.

However, it may also be possible to line the sound duct with a material that has a lower sound dampening effect as compared to the inner insulation material, such as by providing an in comparison thin plastic film to the inner insulation material. As an alternative, the duct material may also or instead comprise a paper or plastic tube section. Using a paper tube section may have advantages from an environmental perspective. In a preferred embodiment a diameter of the sound duct is at least 2 mm, preferably at least 5 mm. The sound duct may have a circular cross section, but the cross section may of course be of any other shape (rectangular, triangular, etc.).

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which.

DETAILED DESCRIPTION

Figure 1:
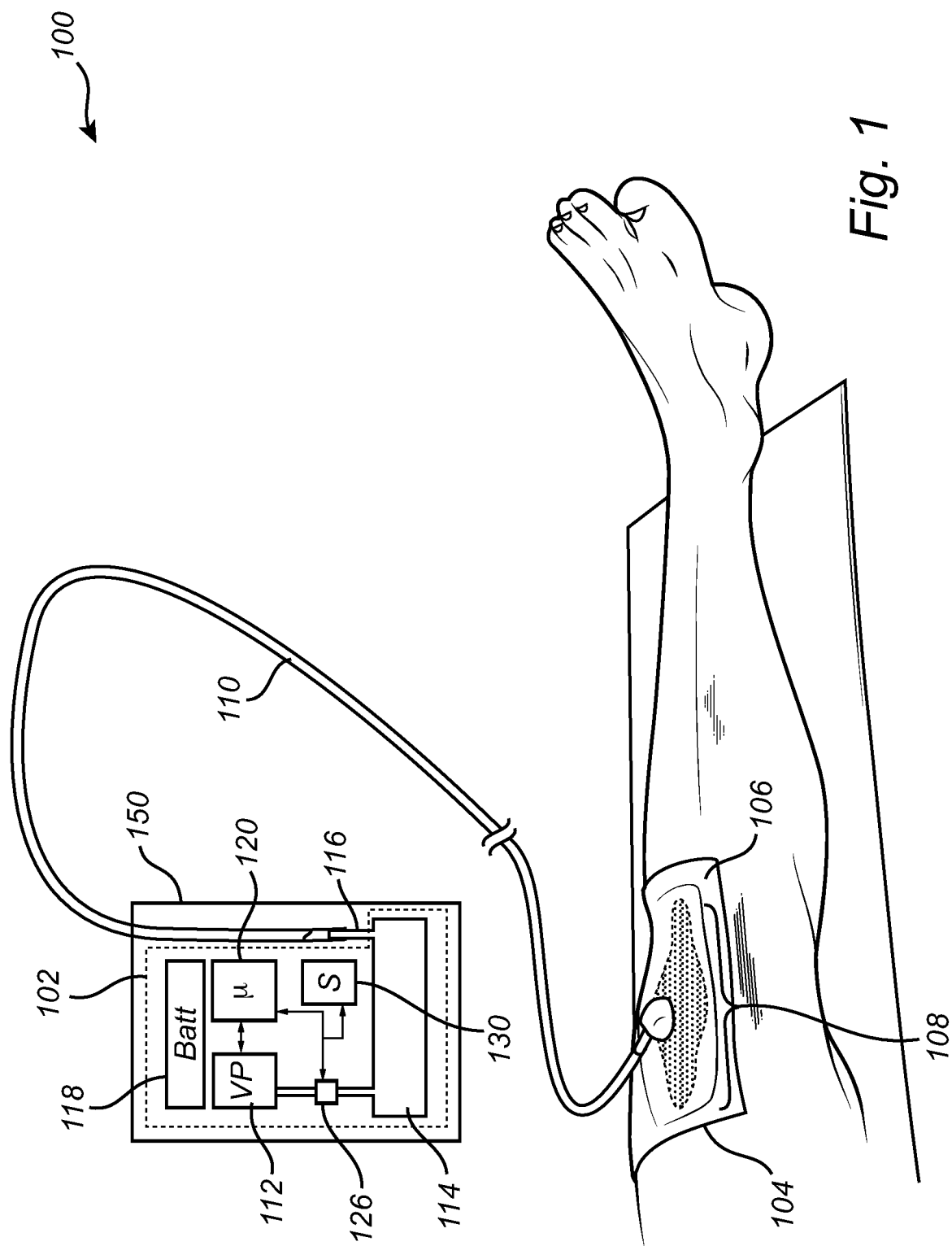
FIG. 1 conceptually illustrates a wound treatment system comprising an NPWT device arranged within a removable enclosure according to the present disclosure, FIG. 2 provides a perspective view of removable enclosure inside which the NPWT device is positioned.

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Turning now to the drawings and to FIG. 1 in particular, there is conceptually illustrated a wound treatment system 100, comprising a NPWT device 102 in accordance with the present disclosure. The wound treatment system 100 further comprises a wound cover 104, the wound cover 104 being adapted to create a sealed space 106 defined in part by a wound surface 108, such as at the skin of a user/person, at or around a wound of the user/person. Additionally, the NPWT device 102 is fluidly connected to the wound cover 104 using e.g. a conduit 110. The conduit 110 may be of any suitable flexible conduit fabricated from elastomeric and/or polymeric materials.

The NPWT device 102 in turn comprises a negative pressure pump 112 adapted for establishing a negative pressure when the negative pressure pump 112 is operable, i.e. in an active state. The negative pressure pump 112 may be any type of pump that is biocompatible and maintains or draws adequate and therapeutic vacuum levels. Preferably, the negative pressure level to be achieved is in a range between about −20 mmHg and about −300 mmHg. In a possible embodiment of the present disclosure, a negative pressure range between about −80 mmHg and about −140 mmHg is used. In a possible embodiment of the present disclosure, the negative pressure pump 112 is either a diaphragm pump or a peristaltic pump, or the like, in which the moving parts draw the mentioned fluid from the wound cover 104.

The negative pressure pump 112 is fluidly connected to a canister 114, the canister 114 also forming part of the NPWT device 102. The canister 114 may be formed from e.g. molded plastic or the like, and possibly being a detachable component of the NPWT device 102. As mentioned above, the canister 114 is preferably at least partly transparent/translucent to permit viewing into the interior of the canister 114 to assist the user in determining the remaining capacity of the canister 114.

For ease of understanding of the following discussion of the present disclosure, it should be understood that the expressions "negative pressure", "sub-atmospheric pressure", "reduced pressure", as used interchangeably herein, generally refer to a pressure less than a local ambient pressure, such as the ambient pressure in a local environment external to a sealed therapeutic environment provided by a wound cover or dressing. In many cases, the local ambient pressure may also be the atmospheric pressure at which a patient is located. Unless otherwise indicated, values of pressure stated herein are gauge pressures. Similarly, references to increases in negative pressure typically refer to a decrease in absolute pressure, while decreases in negative pressure typically refer to an increase in absolute pressure.

An inlet port 116 is formed at the canister 114, for allowing connection to the conduit 110. The inlet port 116 may also be formed elsewhere at the NPWT device 102, however still fluidly connected to the canister 114. The connection between the inlet port 116 and the conduit 110 is a sealed connection, thus ensuring that no leakage is formed at the inlet port 116 during normal operation of the NPWT device 102. The conduit 110 is preferably releasably connected to the inlet port 116 through conventional means including a friction fit, bayonet coupling, snap fit, barbed connector, or the like. The inlet port 116 may be molded/formed from the same material and/or at the same time as forming the canister 114.

The NPWT device 102 further comprises a battery 118 for powering the NPWT device 102. The battery 118 may preferably be of the rechargeable type but may alternatively be arranged to be disposable and thus to be changed once discharged. A specifically adapted battery pack may be used in relation to some embodiment of the present disclosure.

The NPWT device 102 also comprises a control unit 120, electrically connected to the battery 118 and adapted to control an operation of the negative pressure pump 112. The control unit 120 may include a microprocessor, microcontroller, programmable digital signal processor or another programmable device. The control unit 120 may also, or instead, each include an application specific integrated circuit, a programmable gate array or programmable array logic, a programmable logic device, or a digital signal processor. Where the control unit 120 includes a programmable device such as the microprocessor, microcontroller or programmable digital signal processor mentioned above, the processor may further include computer executable code that controls operation of the programmable device.

In line with the present disclosure, the NPWT device 102 further comprises a control circuitry 122 provided externally from the control unit 120 and arranged to generally control the operation of the negative pressure pump 112, specifically for ensuring that the operation of the negative pressure pump 112 may be swiftly terminated in case the NPWT device 102 starts to operate outside of what is considered to be a normal behavior, as has been discussed above.

In addition, the NPWT device 102 comprises at least one pressure sensor 126 arranged in fluid connection with the negative pressure pump 112.

During use of the NPWT device 102, the wound cover 104 is arranged at a wound site of the user/patient, forming the sealed space 106. The conduit 110 is provided to fluidly connect the wound cover 104 to the inlet port 116 of the NPWT device 102. The NPWT device 102 is then activated, e.g. by the user/patient, for example by pressing a start button. When activated, the negative pressure pump 112 will start to evacuate air through the canister 114, the inlet port 116, the conduit 110 and the sealed space 106 formed by the wound cover 104. Accordingly, the negative pressure will be created within the sealed space 106. In case a liquid has been formed at the wound site, this liquid from the wound site may at least partly be "drawn" from the wound site, through the conduit 110, the inlet port 116 and into the canister 114. The amount of liquid (possibly defined as exudate) that is drawn from the wound and collected in the canister will depend on the type of wound that is being treated as well as the type of wound dressing used. For example, in case an absorbent dressing is used, the liquid may be absorbed and collected both in the canister and the wound dressing, whereas if a dressing with no or little absorption capacity is used most or all of the liquid from the wound site may be collected in the canister. A suitable filter member (not shown in FIG. 1) is arranged between the canister 114 and the negative pressure pump 112 to ensure that no fluid is allowed to pass to the negative pressure pump 112 from the canister 114.

In other embodiments (not shown), the NPWT device may be void of a canister, wherein the negative pressure pump is fluidly connected to an absorbent dressing which function to absorb all liquid drawn from the wound.

The NPWT device 102 may also, as indicated above comprise a speaker element 130 and thereto connected circuitry for driving the speaker element 130, where the speaker element 130 is connected to the control unit 120. The speaker element 130 is generally used for informing the patient of a specific state of the NPWT device 102, such as in case there is some form of problem relating to the operation of the NPWT device 102. Such an example may for example be an unwanted leakage in relation to the conduit 110 and/or the wound cover 104 or unwanted blockage of the conduit 110, where the unwanted leakage or blockage is identified by the control unit 120. The speaker element 130 will then be activated and adapted to play a specific and thereto related sound to inform the patient. Further possible dedicated informative sounds may relate to the canister 114 being full, the NPWT device 102 operating in an irregular manner, the battery 118 getting close to completely discharged, etc.

Furthermore, the wound treatment system 100 comprises the removable enclosure 150 according to the present disclosure, for reducing a level of noise generated during operation of the NPWT device 102, such as when the negative pressure pump 112 is activated.

Figure 2:
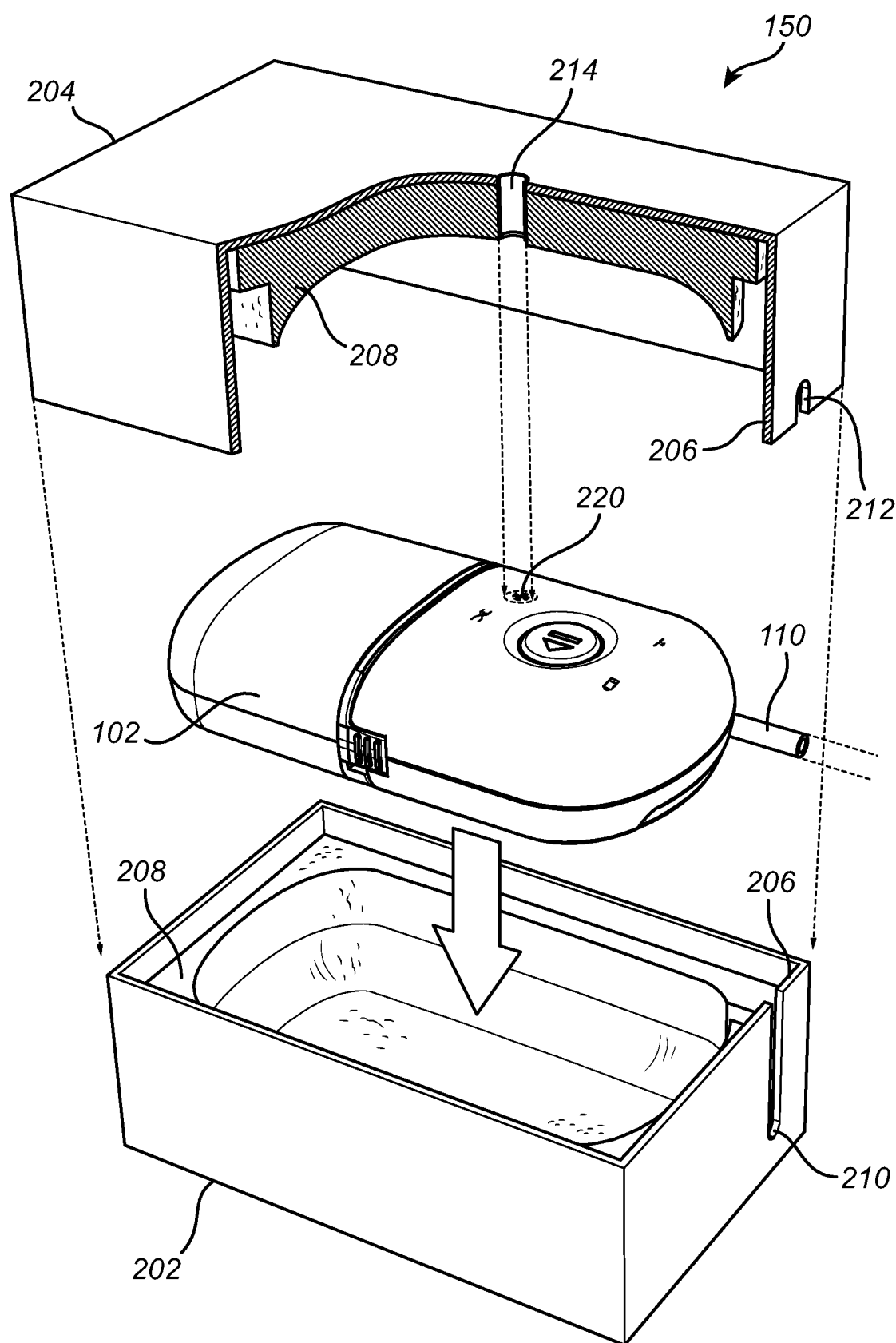
Figure 3A:
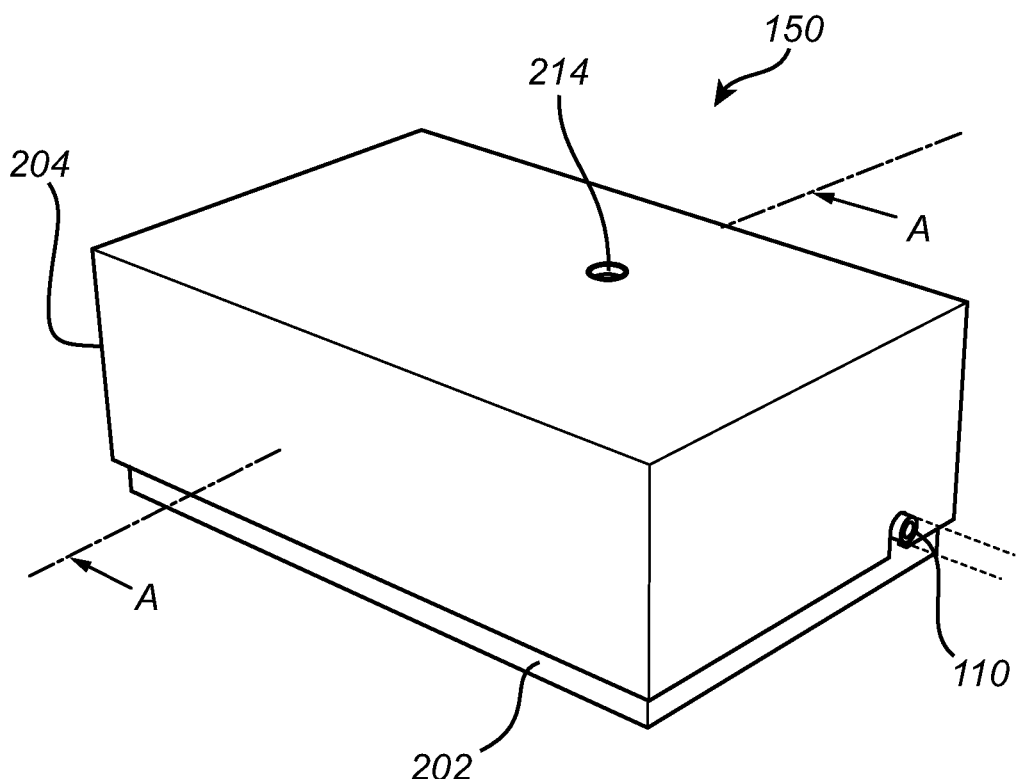
FIGS. 3A and 3B show perspective and cross section views where a first and a second housing section of the removable enclosure have been joined together around the NPWT device.
Figure 3B:
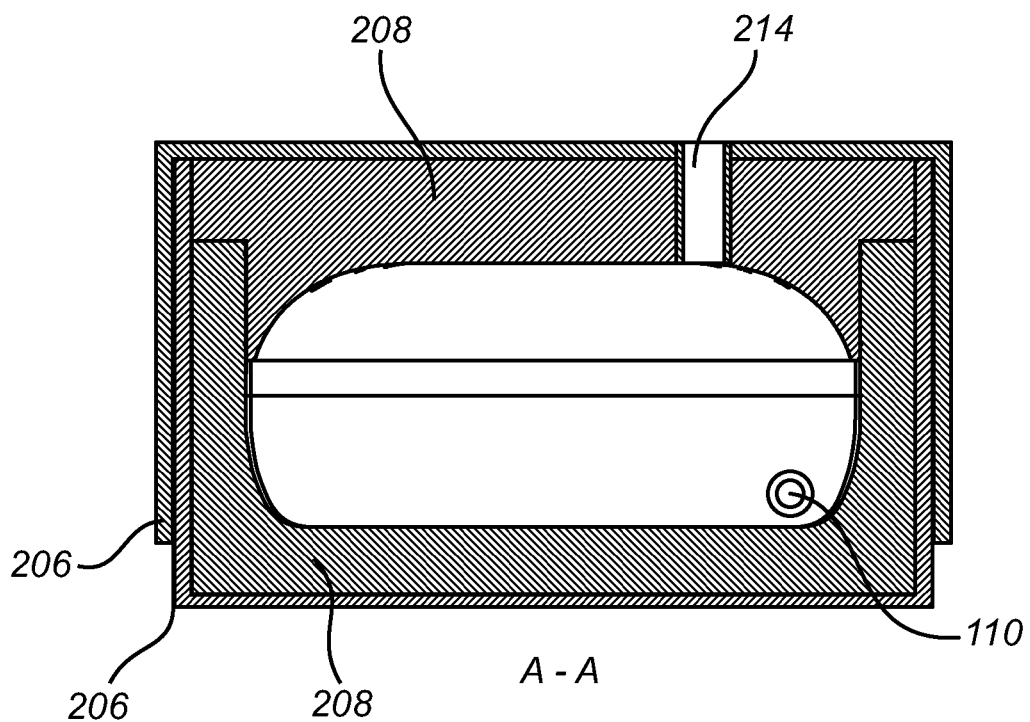

With further reference to FIGS. 2, 3A and 3B, the removable enclosure 150 comprises a first housing section 202 and a second housing section 204. In the illustration as is shown in FIGS. 2, 3A and 3B, the first housing section 202 is shown as a bottom portion of the removable enclosure 150 and the second housing section as a lid portion of the removable enclosure 150. The removable enclosure 150 is in FIGS. 3A and 3B shown to have a rectangular shape with flat sides. It is of course possible to select any shape or form to achieve the desired effect according to the present disclosure.

The first housing section 202, the bottom portion of the removable enclosure 150, is formed from and comprises an outer shell material 206 made from paper and an inner insulation material 208 made from a polymer material that has a cell structure, such as a foam material. Other materials may of course be used with the context and scope of the present disclosure.

The inner insulation material 208 is in turn pre-cut or otherwise shaped (such as by molding) to correspond to a shape of the (bottom of the) NPWT device 102. As can be seen, the inner insulation material 208 is also pre-cut in relation to the conduit 110, and further provided with a slot 210 to allow the conduit 110 to pass through a wall of the first housing section 202.

The second housing section 204, the lid portion of the removable enclosure 150, is also formed from and comprises a corresponding outer shell material 206 made from paper and a corresponding inner insulation material 208 made from a polymer material that has a cell structure, such as a foam material. It is of course possible to use different materials for the lid portion as compared to the bottom portion.

The insulation material 208 of the second housing section 204 is also pre-cut or otherwise shaped to correspond to the shape of the (top of the) NPWT device 102. It may however, depending on the amount of inner insulation material 208 provided in relation to the first housing section 202 to allow the inner insulation material 208 to be essentially flat and to be slightly compressed when the first 202 and the second 204 housing sections are joined together.

In FIG. 2 it is further suggested that also the second housing section 204 is provided with a slot 212, that matches the slot 210 of the first housing section 202 when the first 202 and the second 204 housing sections are joined together.

In the illustration as shown in FIGS. 2, 3A and 3B, it is suggested that the second housing section 204 is completely separate from the first housing section 202 and allowed to extend at an outer surface of the outer shell material 206 of the first housing section 202 when the housing sections are joined together, similar to a shoe box. It may however be possible to allow the housing sections to be partly joined at all time, e.g. arranging the second housing section 204 in a hinged manner as compared to the first housing section 202.

The second housing section 204 is further provided with an elongated sound duct 214 that extends from an inside of the second housing section 204, through the inner insulation material 208 and out through the outer shell material 206. One end of the elongated sound duct 214 is specifically positioned in such a manner that it with a sound outlet position 220 at the NPWT device 102 where sound from the speaker element 130 is "outputted", as is specifically illustrated in FIG. 3. Outputting the sound from the speaker element 130 may be dependent on the implementation selected for the NPWT device 102. In one embodiment, and as illustrated in FIG. 2, the NPWT device 102 is provided with an opening 216 in a housing of the NPWT device 102.

It may however as an alternative be possible to arrange the speaker element 130 (in the form of an actuator) to be connected to the housing of the NPWT device 102, meaning that the housing of the NPWT device 102 will "vibrate" when the speaker element 130. In such an embodiment it could be possible to arrange the first end of the sound duct 214 to be arranged to coincide with a suitable position of the housing of the NPWT device 102. In FIGS. 3A and 3B the sound duct 214 is presented in a preferred embodiment where the sound duct 214 is kept as "short as possible" and perpendicular to a flat outer surface of the second housing section 204, thereby maximining the output of sound generated by the speaker element 130 to an outside of the removable enclosure 150. It is however possible to arrange the sound duct 214 in any other way to achieve the general desired effect of the present disclosure.

Although the figures may show a sequence, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps. Additionally, even though the present disclosure has been described with reference to specific exemplifying embodiments thereof, many different alterations, modifications and the like will become apparent for those skilled in the art.

In addition, variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A removable enclosure for a mobile negative pressure wound therapy (NPWT) device, the NPWT device comprising a negative pressure pump arranged within a housing of the NPWT device and connected to wound cover using a conduit, wherein the removable enclosure comprises:
   a first housing section, and
   a second housing section, wherein the second housing section is arranged to join the first housing section to enclose the NPWT device,
   wherein:
   the first and the second housing section each comprises an outer shell material and an inner insulation material,
   at least one of the first or the second housing section is provided with an opening for passage of the conduit through a wall of the first housing section,
   the second housing section is provided with a sound duct extending through the outer shell material and the inner insulation material, and
   the sound duct is positioned to propagate a sound emitted by a sound generating device comprised with the NPWT device to an outside of the removable enclosure, wherein the sound emitted by the sound generating device is indicative of a state of the NPWT device.

2. The removable enclosure according to claim 1, wherein the sound duct is positioned to coincide with a sound outlet formed at the NPWT device.

3. The removable enclosure according to claim 1, wherein the opening for passage conduit is provides as a slot within a wall of the first housing section.

4. The removable enclosure according to claim 3, further comprising a slot within a wall of the second housing section, wherein the slots align when the first housing section and the second housing section are joined together.

5. The removable enclosure according to claim 1, wherein the outer shell material is of paper or plastic.

6. The removable enclosure according to claim 1, wherein the outer shell material comprises a sandwich structure comprising a paper interior.

7. The removable enclosure according to claim 1, wherein the outer shell material is formed from cardboard.

8. The removable enclosure according to claim 1, wherein the inner insulation material is formed from a polymer material.

9. The removable enclosure according to claim 8, wherein the polymer material has a cell structure.

10. The removable enclosure according to claim 1, wherein the sound duct comprises a duct material and the duct material is different from the inner insulation material.

11. The removable enclosure according to claim 10, wherein the duct material comprises at least one of a paper or plastic tube section.

12. The removable enclosure according to claim 1, wherein a diameter of the sound duct is at least 5 mm.

13. The removable enclosure according to claim 1, wherein a thickness of the inner insulation material is at least 10 mm.

14. The removable enclosure according to claim 1, wherein the outer shell material and an inner insulation material and the inner insulation material is selected to attenuate noise from the negative pressure pump, during operation of the NPWT device, with at least 4 dBa.

15. The removable enclosure according to claim 1, wherein a thickness of the outer shell material is at least 2 mm.

16. The removable enclosure according to claim 1, wherein the outer shell material and an inner insulation material and the inner insulation material is selected to attenuate noise from the negative pressure pump, during operation of the NPWT device, with at least 6 dBa.

17. The removable enclosure according to claim 1, wherein the sound duct has a circular cross section.

18. The removable enclosure according to claim 1, wherein the inner insulation material includes a foam material.

19. The removable enclosure according to claim 1, wherein the inner insulation material is formed to match a shape of the NPWT device.

20. A wound treatment system, comprising:
   mobile negative pressure wound therapy (NPWT) device, and
   a removable enclosure according to claim 1.

* * * * *